US00PP29775P3

(12) United States Plant Patent
Uchneat

(10) Patent No.: US PP29,775 P3
(45) Date of Patent: Oct. 23, 2018

(54) *SALVIA* PLANT NAMED 'SGRPU03-0'

(50) Latin Name: *Salvia splendens*
Varietal Denomination: SGRPU03-0

(71) Applicant: Michael Uchneat, Bellefonte, PA (US)

(72) Inventor: Michael Uchneat, Bellefonte, PA (US)

(73) Assignee: Garden Genetics, LLC, Bellefonte, PA (US)

( * ) Notice: Subject to any disclaimer, the term of this patent is extended or adjusted under 35 U.S.C. 154(b) by 33 days.

(21) Appl. No.: 15/530,309

(22) Filed: Dec. 21, 2016

(65) Prior Publication Data

US 2018/0177107 P1 Jun. 21, 2018

(51) Int. Cl.
*A01H 5/02* (2018.01)
*A61K 36/537* (2006.01)

(52) U.S. Cl.
USPC ..... Plt./475
CPC ..... *A01H 5/02* (2013.01); *A61K 36/537* (2013.01)

(58) Field of Classification Search
USPC ..... Plt./475
See application file for complete search history.

*Primary Examiner* — Keith O Neal Robinson
(74) *Attorney, Agent, or Firm* — Cassandra Bright

(57) ABSTRACT

A new and distinct *Salvia* cultivar named 'SGRPU03-0' is disclosed, characterized by vigorous plants with a large, upright form and long flowering period. Flowers are dark purple. Calyces are persistent and retain their dark purple color. The new variety is a *Salvia splendens*, normally produced as an outdoor garden or container plant.

2 Drawing Sheets

Figure 1:
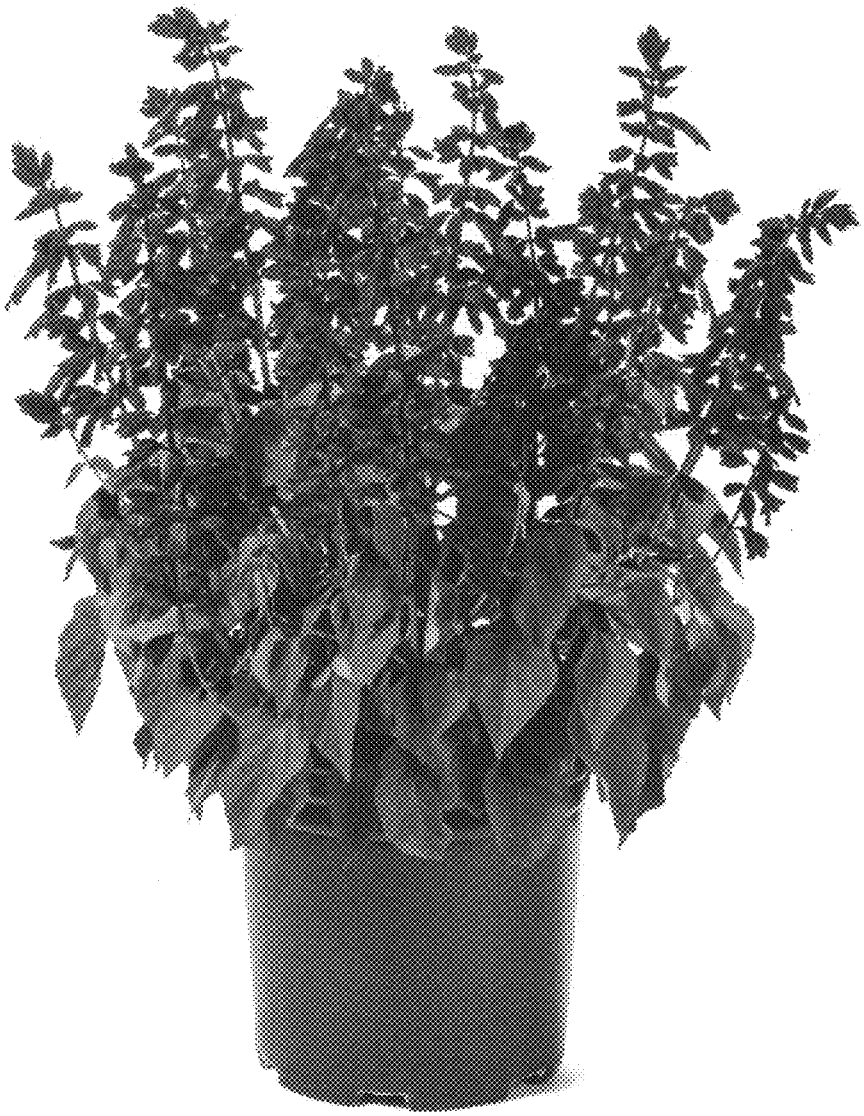

Latin name of the genus and species: *Salvia splendens*.
Variety denomination: 'SGRPU03-0'.

BACKGROUND OF THE INVENTION

The new *Salvia* cultivar is a product of a planned breeding program conducted by the inventor, Michael Uchneat in Bellefonte, Pa. The objective of the breeding program was to produce new *Salvia splendens* varieties with large, upright plant habits in a range of flower colors and with persistent calyx. The crossing resulting in this new variety was made during May of 2012.

The seed parent variety is an unpatented, proprietary, *Salvia splendens* referred to as '16666-1'. The pollen parent is the unpatented proprietary *Salvia splendens* variety referred to as '16651-3'. The new variety was identified as a potentially interesting selection in September 2012, at a greenhouse in Bellefonte, Pa.

Asexual reproduction of the new cultivar 'SGRPU03-0' by vegetative cuttings was first performed during October of 2012, at a research greenhouse in Bellefonte, Pa. Subsequent propagation has shown that the unique features of this cultivar are stable and reproduced true to type on successive generations.

SUMMARY OF THE INVENTION

The cultivar 'SGRPU03-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SGRPU03-0' These characteristics in combination distinguish 'SGRPU03-0' as a new and distinct *Salvia* cultivar:

1. Vigorous, large, upright plant larger than most *Salvia splendens* in the trade.
2. Long flowering period from young plant until frost.

3. Calyx are persistent, and color of the calyx is retained.
4. Deep purple calyx and purple corolla.

PARENT COMPARISON

Plants of the new cultivar 'SGRPU03-0' are similar to plants of the seed parent in most horticultural characteristics, however, plants of the new cultivar 'SGRPU03-0' differ in the following:

1. The new variety begins flower early Spring, the seed parent begins flowering much later.
2. Size of the new variety is considerably larger than the seed parent.
3. Foliage of the seed parent is darker than foliage of the new variety.

Plants of the new cultivar 'SGRPU03-0' are similar to plants of the pollen parent in most horticultural characteristics, however, plants of the new cultivar 'SGRPU03-0' differ in the following:

1. The new variety has deep purple flowers, the pollen parent has red flowers.
2. The new variety produces more branches than the pollen parent.

COMMERCIAL COMPARISON

Plants of the new cultivar 'SGRPU03-0' can also be compared to the commercial variety *Salvia splendens* 'Saucy Purple', unpatented. These varieties are similar in most horticultural characteristics; however 'SGRPU03-0' differs in the following:

1. The new variety has darker purple flower color than this comparator.
2. A higher percentage of calyx persistence is observed in the new variety.
3. Foliage of the new variety is darker green.
4. The new variety is not sterile, whereas 'Saucy Purple' appears to be sterile.

Plants of the new cultivar 'SGRPU03-0' can also be compared to the commercial variety *Salvia splendens* 'Lighthouse Purple', unpatented. These varieties are similar in most horticultural characteristics; however 'SGRPU03-0' differs in the following:

1. The new variety has a darker purple flower color.
2. Flowering spikes of the new variety are longer than those of 'Lighthouse Purple'.

BRIEF DESCRIPTION OF THE PHOTOGRAPHS

The accompanying photograph in FIG. 1 illustrates in full color a typical plant of 'SGRPU03-0' grown in a greenhouse, in Santa Paula, Calif., in a commercial 10 inch container.

Figure 2:
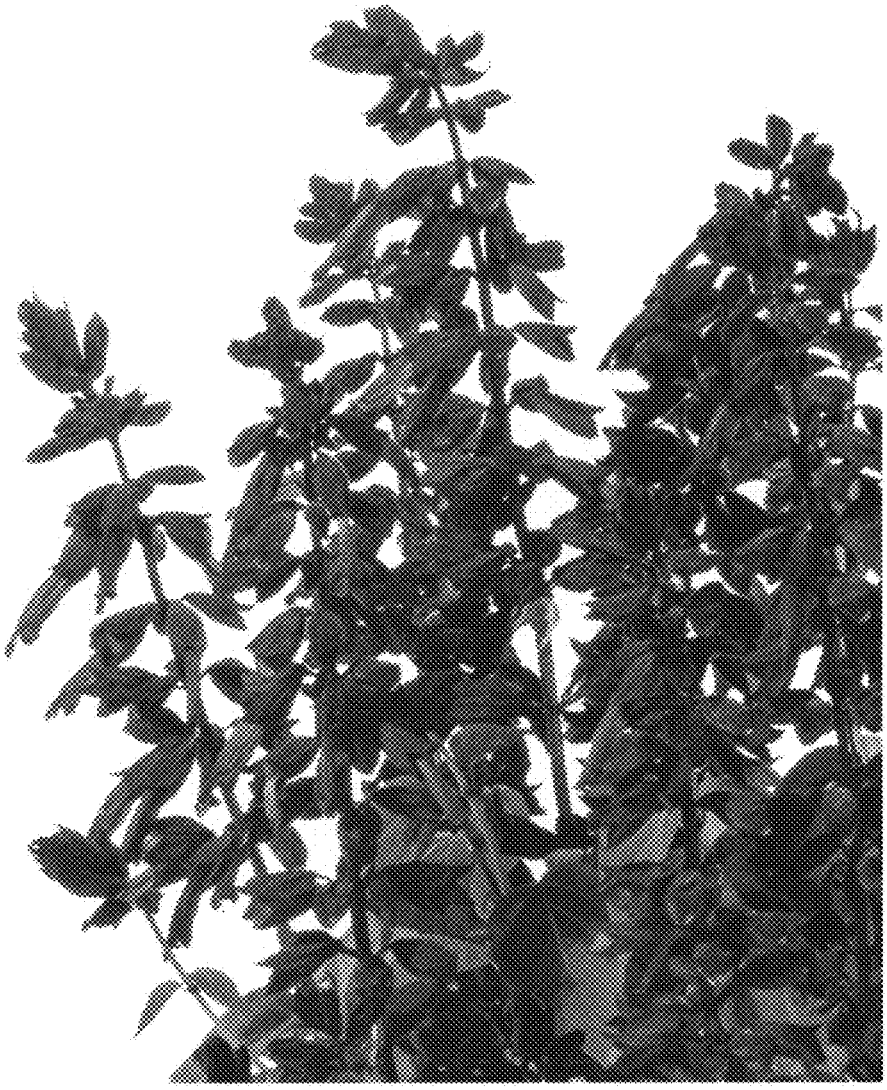

FIG. 2 illustrates in full color typical flowering spikes of 'SGRPU03-0'. Age of the plant photographed is approximately 3 months from 3 rooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SGRPU03-0' plants grown in a greenhouse in Santa Paula, Calif. The growing temperature ranged from approximately 10° C. to 30° C. The greenhouse is unshaded, giving bright, normal sunlight conditions. Measurements and numerical values represent averages of typical plant types.

Botanical classification: *Salvia splendens* 'SGRPU03-0'.

PROPAGATION

Root description: Fine, densely fibrous. Colors include Green-White 157D on new growth and Orange-White 159C, Grey-Brown 199B and 199C for older roots.

PLANT

Pot size of plant described: 1 gallon pot.

Height: Approximately 25 cm to top of foliage. Approximately 50 cm to top of flowering plane. Measured from soil level of pot.

Plant spread: Approximately 55 cm.

Growth habit: Upright.

Growth rate: Rapid.

Branching characteristics: Moderately well branched. Approximately 2 to 4 branches emerging from a pinch, which branch into another 2 to 4 primary lateral branches.

Length of primary lateral branches: Approximately 12 cm.

Diameter of lateral branches: Approximately 0.5 cm.

Quantity of lateral branches: About 16 to 24.

Stem:

- *Color*.—Near RHS Green 137A. Nodes lightly flushed Violet-Blue N92A.
- *Texture*.—Pubescent and ribbed.

Internode length: Average range 2.5 to 4.0 cm.

Age of plant described: Approximately 20 weeks from 3 rooted cuttings.

FOLIAGE

Leaf:

- *Arrangement*.—Opposite.
- *Quantity*.—Average range 6 to 12 fully expanded per main branch.
- *Average length*.—Approximately 9.5 cm. including petiole.
- *Average width*.—Approximately 4.0 cm.
- *Shape of blade*.—Deltoid.
- *Apex*.—Acute.
- *Base*.—Truncate.
- *Variegation*.—Absent.
- *Attachment*.—Stalked.
- *Margin*.—Denate.
- *Texture of top surface*.—Matte, glabrous. Shallow reticulate.
- *Texture of bottom surface*.—Matte, glabrous, reticulate.
- *Color*.—Young foliage upper side: Near RHS Green 139A. Young foliage under side: Near RHS Green 137B. Mature foliage upper side: Near RHS Green 139A. Mature foliage under side: Near RHS Green 138A.
- *Venation*.—Type: Reticulate. Venation color upper side: Near RHS Green 143C. Venation color under side: Near RHS Green 143C.
- *Petiole*.—Average Length: Approximately 3.9 cm. Diameter: Approximately 0.2 cm. Color: Near Yellow-Green 146 A.

FLOWER

Natural flowering season: Flowering from early Spring until the first heavy frost.

Inflorescence type and habit: Flowers arranged in verticillasters on spikes.

Flower longevity on plant: Individual flowers last approximately 7 to 10 days on the plant. Each spike lasts approximately 4 to 6 weeks with flowers. Corolla self cleaning, calyx persistent.

Quantity of flowers: About 12 to 16 buds and 24 to 36 fully opened flowers per spike, at one time. Mature plants have approximately 20 to 30 spikes.

Spike size:

- *Diameter*.—Approximately 11.0 cm.
- *Height*.—Approximately 18.0 cm.

Individual flowers:

Size:

- *Diameter*.—Approximately 1.0 cm.
- *Length*.—Approximately 4.2 cm.
- *Inflorescence internode*.—6-9 mm.
- *Number of florets per node*.—3 per node.
- *Fragrance*.—Very faint floral scent.

Corolla:

- *Petal arrangement*.—The corolla is sympetalous and typically bilabiate with 2 small, fully fused lobes forming a single upper lip and 3 larger fused lobes forming a lower lip.
- *Margin*.—Entire.
- *Tip shape*.—Upper lip tip obtuse, lower lip tip retuse.
- *Overall length*.—4 cm.
- *Length*.—Upper lip Approximately 0.8 cm. Lower lip Approximately 0.6 cm. Tube length Approximately 3.0 cm.

*Width*.—Upper lip: Approximately 0.6 cm, lower lip Approximately 0.9 cm. Tube width: Approximately 0.8 cm.

*Texture*.—Upper lip: Glabrous all surfaces. Lower lip: Glabrous all surfaces.

Color:

*Upper lip*.—When opening: Inner surface: Near RHS Purple N79A, but darker. Outer surface: Near RHS Purple N79A, but darker. Fully opened: Inner surface: Near RHS Purple N79A, but darker. Outer surface: Near RHS Purple N79A, but darker. Fading: Inner surface: Near RHS Red-Purple 59A. Outer surface: Near RHS Red-Purple 59A.

Color:

*Lower lip*.—When opening: Inner surface: Near RHS Purple N79A, but darker. Outer surface: Near RHS Purple N79A, but darker. Fully opened: Inner surface: Near RHS Purple N79A, but darker. Outer surface: Near RHS Purple N79A, but darker. Fading: Inner surface: Near RHS Red-Purple 59A. Outer surface: Near RHS Red-Purple 59A.

Color:

*Tube*.—When opening: Inner surface: Near RHS Purple N79A, but darker. Outer surface: Near RHS Purple N79A, but darker. Fully opened: Inner surface: Near RHS Purple N79A, but darker. Outer surface: Near RHS Purple N79A, but darker, streaked Violet 84D. Fading: Inner surface: Near RHS Red-Purple 59A. Outer surface: Near RHS Red-Purple 59A, streaked Purple 76D.

Bud: Flower bud includes immature calyx which completely surrounds immature corolla.

*Shape*.—Ovoid.

*Length*.—Approximately 2.0 cm.

*Diameter*.—Approximately 0.8 cm.

*Color*.—Near RHS Purple N77A.

Calyx:

*Length*.—Approximately 2.4 cm.

*Diameter*.—Approximately 0.9 cm.

*Shape*.—Tubular.

Sepals:

*Shape*.—Quantity per flower: 3, fused to form a tube. Unfused apex.

*Length*.—Approximately 0.8 cm unfused portion.

*Width*.—Approximately 1.0 cm.

*Margin*.—Entire.

*Apex*.—Short apiculate.

*Texture*.—Softly pubescent.

*Color*.—Immature: Near RHS Purple N77A. Mature: Near RHS Purple N77A.

Peduncle:

*Length*.—Average 5.0 cm.

*Diameter*.—0.4 cm.

*Color*.—Near RHS Yellow-Green 147A, flushed Greyed-Purple N187A.

*Orientation*.—Straight, approximately 25 degree angle from center of plant.

*Strength*.—Strong.

*Texture*.—Softly pubescent, ridged.

Pedicels:

*Length*.—Average range 0.3 to 0.8 cm.

*Diameter*.—0.1 cm.

*Color*.—Near RHS Purple N79A.

*Orientation*.—Straight, approximately 90 degree angle from attachment.

*Strength*.—Flexible.

*Texture*.—Pubescent.

REPRODUCTIVE ORGANS

Stamens:

*Number*.—2.

*Filament length*.—Approximately 3.5 cm.

*Filament color*.—Near RHS White N155A.

Anthers:

*Shape*.—Linear.

*Length*.—0.2 cm.

*Color*.—Near RHS Purple N79A.

*Pollen*.—Scant pollen observed, colored near RHS White N155A.

Pistil:

*Number*.—1.

*Length*.—Approximately 4.0 cm.

*Style*.—Length: Approximately 3.7 cm. Color: Near RHS White N155C.

*Stigma*.—Shape: Forked. Color: Near RHS Purple N77A. Ovary: Colored near RHS White N155C, oblong, approximately 0.3 cm long and 0.2 in diameter.

OTHER CHARACTERISTICS

Seeds and fruits: Fruit is a paper capsule, approximately 5 mm long and 3 mm wide. Colored near Grey-Purple N187D. Typically 4 seeds per pod, approximately 2 mm long and 2 mm wide. Colored near Brown 200B.

Disease/pest resistance: Neither resistance nor susceptibility to pathogens and pests common to *Salvia splendens* have been observed. The most common disease is powdery mildew (*Golovinomyces chicoracearum*, various *Odium* species). Common pests include various species of *Aphis* and *Meloidogyne*.

Temperature tolerance: The new variety is a tender herbaceous perennial, tolerating temperatures within USDA zones 10 to 11.

What is claimed is:

1. A new and distinct cultivar of *Salvia* plant named 'SGRPU03-0' as herein illustrated and described.

* * * * *